(12) United States Patent
Tamura et al.

(10) Patent No.: US 6,690,461 B1
(45) Date of Patent: Feb. 10, 2004

(54) METHOD FOR DISPLAYING MICROARRAY INFORMATION

(75) Inventors: Takuro Tamura, Kanagawa (JP); Jyunji Yoshii, Kanagawa (JP); Katsuya Mizuno, Kanagawa (JP)

(73) Assignee: Hitachi Software Engineering Co., Ltd., Kanagawa (JP)

(*) Notice: Subject to any disclaimer, the term of this patent is extended or adjusted under 35 U.S.C. 154(b) by 252 days.

(21) Appl. No.: 09/806,249

(22) PCT Filed: Jul. 19, 2000

(86) PCT No.: PCT/JP00/04840
§ 371 (c)(1),
(2), (4) Date: Mar. 27, 2001

(87) PCT Pub. No.: WO01/07898
PCT Pub. Date: Feb. 1, 2001

(30) Foreign Application Priority Data

Jul. 27, 1999 (JP) .............................. 11-212326

(51) Int. Cl.$^7$ ............................ G10J 3/30; G10N 21/76
(52) U.S. Cl. ..................... 356/311; 436/172; 435/288.7; 382/168; 422/52
(58) Field of Search ................................ 356/311, 318, 356/401; 430/31, 56; 435/288.7, 287.2; 422/52, 82.05, 82.07, 82.08; 436/172; 345/418, 523; 382/128, 168; 702/155

(56) References Cited

U.S. PATENT DOCUMENTS 5,744,320 A * 4/1998 Sherf et al. ................. 356/4.01
5,798,263 A * 8/1998 Wood et al. .............. 435/288.7
5,907,820 A * 5/1999 Pan ............................ 702/155

FOREIGN PATENT DOCUMENTS

| JP | 2-168161 | 6/1990 |
|----|----------|--------|
| JP | 2-271827 | 11/1990 |
| JP | 110-75087 | 3/1999 |
| JP | 11-342000 | 8/1999 |

* cited by examiner

*Primary Examiner*—Andrey Chang

(74) *Attorney, Agent, or Firm*—Reed Smith LLP; Stanley P. Fisher, Esq.; Juan Carlos A. Marquez, Esq.

(57) ABSTRACT

A method for displaying microarray information by which unknown but useful information is extracted from a mass amount of sample information obtained with microarrays. Luminescent intensity information of sample spots obtained with the microarrays is standardized for each microarray and displayed as a graph as a difference from the standardized luminescent intensity of a sample spot of interest. Accordingly, information can be compared without being influenced by a difference of experiment status between the microarrays or a difference of physical properties between the samples. A three-dimensional graph is displayed by sorting the set of samples and the set of microarrays to which the sample spots belong, under predetermined conditions, and assigning the set of sorted samples and the set of sorted microarrays to X-axis and Y-axis, and the accumulated luminescence intensity to Z-axis.

8 Claims, 8 Drawing Sheets

X: Display of microarray plane

Y: Display of sample plane

81: Designated sample (reference sample)

METHOD FOR DISPLAYING MICROARRAY INFORMATION

This application claims priority to PCT application Ser. No. PCT/JP00/04840, filed Jul. 19, 2000, and Japanese Application Serial No. 212326/1999, filed Jul. 27, 1999.

TECHNICAL FIELD

The present invention relates to processing of microarray experiment data, particularly, to a method for visually displaying useful microarray information.

BACKGROUND ART

Conventionally, as a method for obtaining useful information from data resulting from experiments using microarrays (also referred to as biochips), the following methods are known. Specifically, a method in which sample spots extracted and sorted under specific conditions are displayed as an image of pixels representing values standardized for each microarray, and a method in which sample spots are classified based on a statistical analysis (a clustering analysis) of luminescent intensity data of the sample spots between multiple microarrays.

Although conventional methods are effective in providing intuitive information via an image of a collection of numerous samples immobilized on microarrays or in providing statistical information by a clustering analysis, they are not always effective in finding out information that is important in terms of molecular biology, which is present in a scarce amount buried in the huge amount of microarray experiment information. It has not been long since microarrays have begun to be used in molecular biological experiments, and in order to elucidate facts unanticipated by users from the microarray information, there is a need of obtaining means for displaying information from various points of view.

The objective of the present invention is to realize a user interface which is capable of effectively processing a huge amount of microarray information and displaying it as a graph, to achieve a system capable of discovering scarce but important information in terms of molecular biology buried in the huge amount of microarray information.

DISCLOSURE OF THE INVENTION

The present invention is provided with: a "microarray primary database" for accumulating information of spots immobilized on microarrays and luminescent intensity data of the numerous sample spots obtained by a microarray analysis; a "micoarray data extracting/processing program" for extracting, under specific conditions, a data set including a plurality of samples and processing it for displaying a graph; a "micoarray information display program" for displaying a three-dimensional graph where the sample spots and the microarrays sorted under various conditions are assigned to X- and Y-axes and luminescent intensities to Z-axis; a method for not missing any signals in the huge amount of information in displaying the three-dimensional graph produced by the microarray information display program; and a cache processing software for a fast display of the information.

The luminescent intensity information of the sample spots obtained with the microarrays is standardized for each microarray. Then, the differences of the standardized luminescent intensities of the sample spots from a standardized luminescent intensity of a sample spot of interest are displayed as a graph. Accordingly, information can be compared without being biased by a difference between the microarrays (biochips) caused by experimental errors or a difference between samples caused by physical properties. Selection of parameters for displaying without missing any important information in the data or for displaying information from various points of view can be realized with a user interface.

A method of the present invention for displaying microarray information by which information of accumulated luminescent intensities of numerous sample spots obtained by a microarray analysis is displayed, comprises the steps of: selecting a set of samples as subjects of a test; acquiring accumulated luminescent intensities of the sample spots on each of microarrays, the sample spot corresponding to the set of samples; sorting the set of samples and the set of microarrays to which the sample spots belong, under predetermined conditions; and displaying a three-dimensional graph by assigning the set of sorted samples and the set of sorted microarrays to X-axis and Y-axis, and the accumulated luminescent intensities to Z-axis.

Preferably, the accumulated luminescent intensities are based on standardized luminescent intensities which have undergone a first standardization using a control spot located on each microarray for a purpose of eliminating experimental errors within the microarray to which the sample spot belongs, and a second standardization using a standard marker spot located on each microarray for the purpose of eliminating experiment errors between the microarrays and for the purpose of equalizing an intentionally adjusted range of luminescent intensities.

Preferably, the standardized accumulated luminescent intensities have undergone, in addition to the first and second standardizations, a third standardization in view of the luminescent intensity ranges between the samples based on the accumulated luminescent intensities of the sample spots belonging to the same sample.

In displaying microarray information, it is advantageous that the set of samples are sorted according to their accumulated luminescent intensities on a specific microarray. In addition, it is advantageous that after the set of samples are sorted according to their accumulated luminescent intensities on a specific microarray, the set of microarrays are sorted according to a total difference of the accumulated luminescent intensities of their samples from that of the specific micoarray. Alternatively, it is advantageous that the set of microarrays are sorted according to an accumulated luminescent intensity of a specific sample. In addition, it is also advantageous that after the set of microarrays are sorted according to an accumulated luminescent intensity of a specific sample, the set of samples are sorted according to a total difference of the accumulated luminescent intensities on the microarrays from that of the specific sample. In either case, the accumulated luminescent intensities are preferably standardized by the first, second or third method. The total difference may be a standard deviation or a mean deviation of the accumulated luminescent intensities.

Furthermore, it is also advantageous that a two-dimensional graph is displayed by slicing out a cross-sectional plane from the three-dimensional graph displayed by the method for displaying microarray information.

According to the present invention, meaningful information can visually be obtained from luminescent intensity information obtained with microarrays. Even an extremely small signal included in the mass amount of information can be displayed without being missed.

BRIEF DESCRIPTION OF THE DRAWINGS

FIG. 1(b) is a schematic plan view of the produced microarrays; and FIG. 1(c) is a schematic view showing the microarray after a reaction such as a hybridization reaction.

BEST MODES FOR CARRYING OUT THE INVENTION

The present invention will be described in more details with reference to the accompanying drawings.

Figure 1:
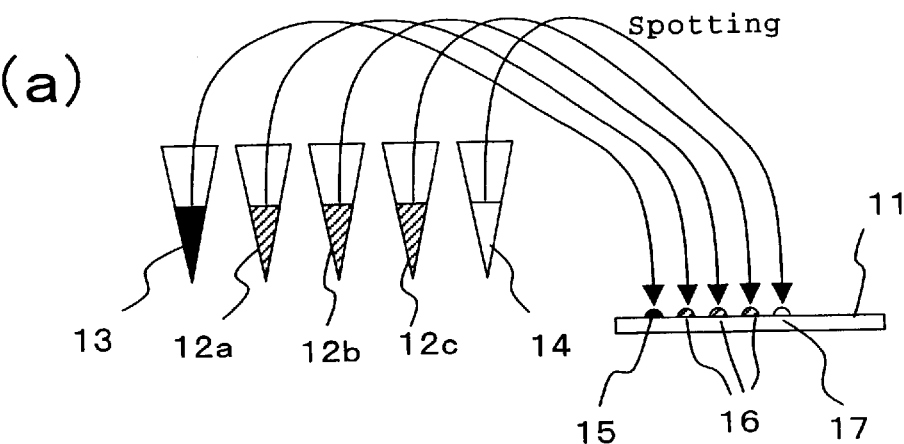
FIGS. 1(*a*) to 1(*c*) are illustrations showing exemplary microarrays, where FIG. 1(*a*) is a schematic view showing a step of producing the microarray.
Figure 1:
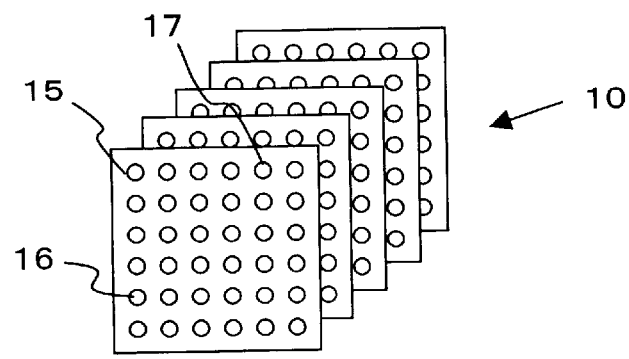
Figure 1:
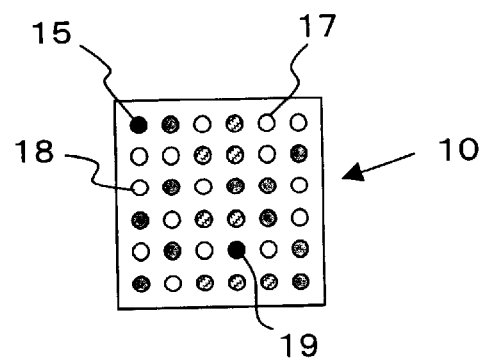

FIGS. 1(a) to 1(c) are illustrations showing exemplary microarrays. FIG. 1(a) is a view schematically showing a step of producing a microarray; FIG. 1(b) is a schematic plan view of the produced microarrays; and FIG. 1(c) is a schematic view showing the microarray after a reaction such as a hybridization reaction.

The microarray 10 as schematically shown in FIG. 1(a) is obtained by high-densely spotting and immobilizing prepared samples 12a, 12b, 12c, . . . such as various kinds of cDNAs, oligonucleotides or proteins on a carrier 11 such as a glass plate with a microarray producing apparatus. The samples immobilized on the microarray 10 are referred to as sample spots 16. As shown in FIG. 1(b), a plurality of microarrays 10 having the same kinds of samples immobilized thereon are produced to perform experiments under different conditions on the respective microarrays. Herein, experiments refer to hybridization experiments using various color-labeled complementary DNAS/RNAs present in unknown proportions as experiment subjects for cDNA or oligonucleotide microarrays, or antigen-antibody reaction experiments using various color-labeled antigens/antibodies present in unknown proportions as experiment subjects for protein microarrays. These experiments are conducted to find out the presence or absence of a color-labeled molecule under different conditions via a specific interaction with a specific sample molecule immobilized on the microarrays.

As shown in FIG. 1(c), after the experiments, each sample spot on the microarray 10, depending on a subject of the experiment, may either be a spot 19 that interacted with a color-labeled molecule or a spot 18 that did not interact with the color-labeled molecule. The spots 19 that underwent the interaction can further be grouped as spots that interacted with a large amount of the color-labeled molecule or spots that interacted with a little amount of the color-labeled molecule. The luminescent intensity of each sample spot on the microarray 10 is read with a microarray reader and numerically expressed as an accumulated value of the luminescent intensities on each spot region, to be used as a measurement value for processing information.

For experiments using the microarrays 10, a particular spot is provided on each microarray 10 for the purpose of adjusting errors in the measurement values resulting from a production error of the microarrays 10 or the sample spots 16 in each experiment, a preparation error of the experiment subjects or an error of experiment conditions. Specifically, a typical sample is selected, prepared like other samples but without color-labeling as a control 14 and spotted, thereby producing a control spot 17. In addition, a sample that is known to interact in the same manner with one of the experiment subject molecules in every experiments is selected, prepared like other samples as a standard marker 13 and spotted, thereby producing a standard marker spot 15. The luminescent intensities of these particular spots 15 and 17 are also read with the microarray reader like those of other sample spots 16 and numerated as accumulated values of the luminescent intensities on the respective spot regions, to be used as measurement values for processing information.

Figure 2:
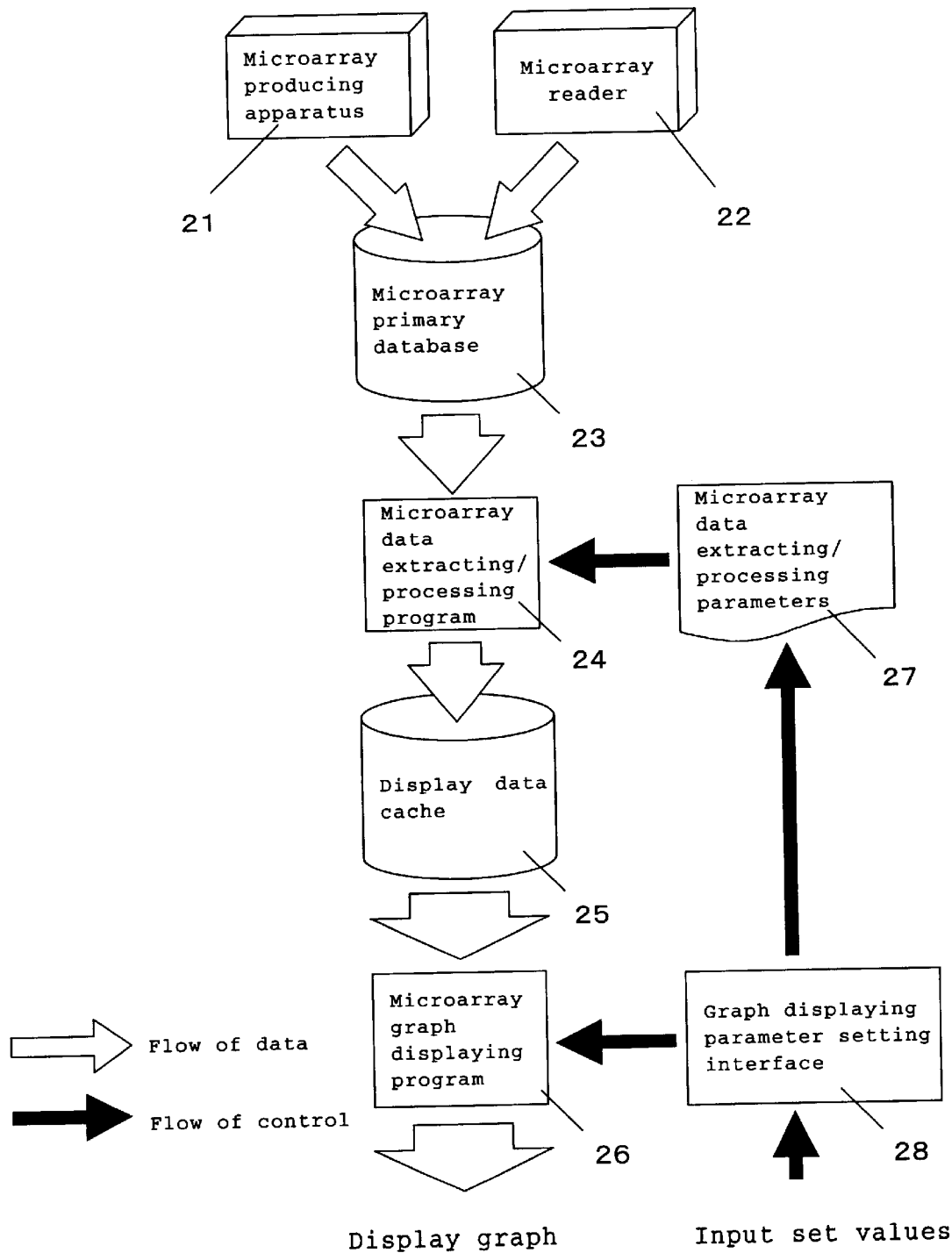
FIG. 2 is a block diagram showing a system for displaying microarray information according to one embodiment of the present invention.

FIG. 2 is a block diagram showing a configuration of a system for displaying microarray information according to one embodiment of the present invention.

In producing the microarray 10, a microarray producing apparatus 21 gives, to a microarray primary database 23, information as to which sample, control or standard marker has been spotted at which coordinates on the microarray 10. Then, a microarray reader 22 reads luminescent intensities of the spots present on the microarray after the experiment. The obtained measurement values are stored in the microarray primary database 23. The measurement value of the luminescent intensities of each spot is stored in the microarray primary database 23 while being collated with and correlated to the pre-stored coordinates information of the sample spots, the control spot or the standard marker spot on the microarray.

A microarray data extracting/processing program 24 extracts, from the microarray primary database 23, data of sample spots suitable for the conditions set as microarray data extracting/processing parameters 27 and processes that data according to the conditions set via a graph displaying parameter setting interface 28.

A microarray graph displaying program 26 acquires the data of sample spots processed by the microarray data extracting/processing program 24 according to the settings of the graph displaying parameter setting interface 28 and generates a graph. The microarray graph displaying program 26 acquires the processed data of the sample spots via a display data cache 25. In other words, the processed sample spot data is temporarily accumulated in the display data cache 25. When the microarray graph displaying program 26 demands for the processed sample spot data, data is provided without needing the microarray data extracting/processing program 24. The capacity of the display data cache 25 to accumulate the data can be set by the user. When the cache is full, data which has been stored in the cache for the longest period since the last demand by the microarray graph displaying program 26 is abandoned to store the latest data in the cache.

The microarray data extracting/processing parameters 27 are produced in a graph displaying parameter setting interface 28. Conditions for displaying a graph can be altered by inputting setting values via the graph displaying parameter setting interface 28 while confirming the graph displayed by the microarray graph displaying program 26. In other words, data of sample spots can be processed on demand, expressed as a graph and confirmed.

Figure 3:
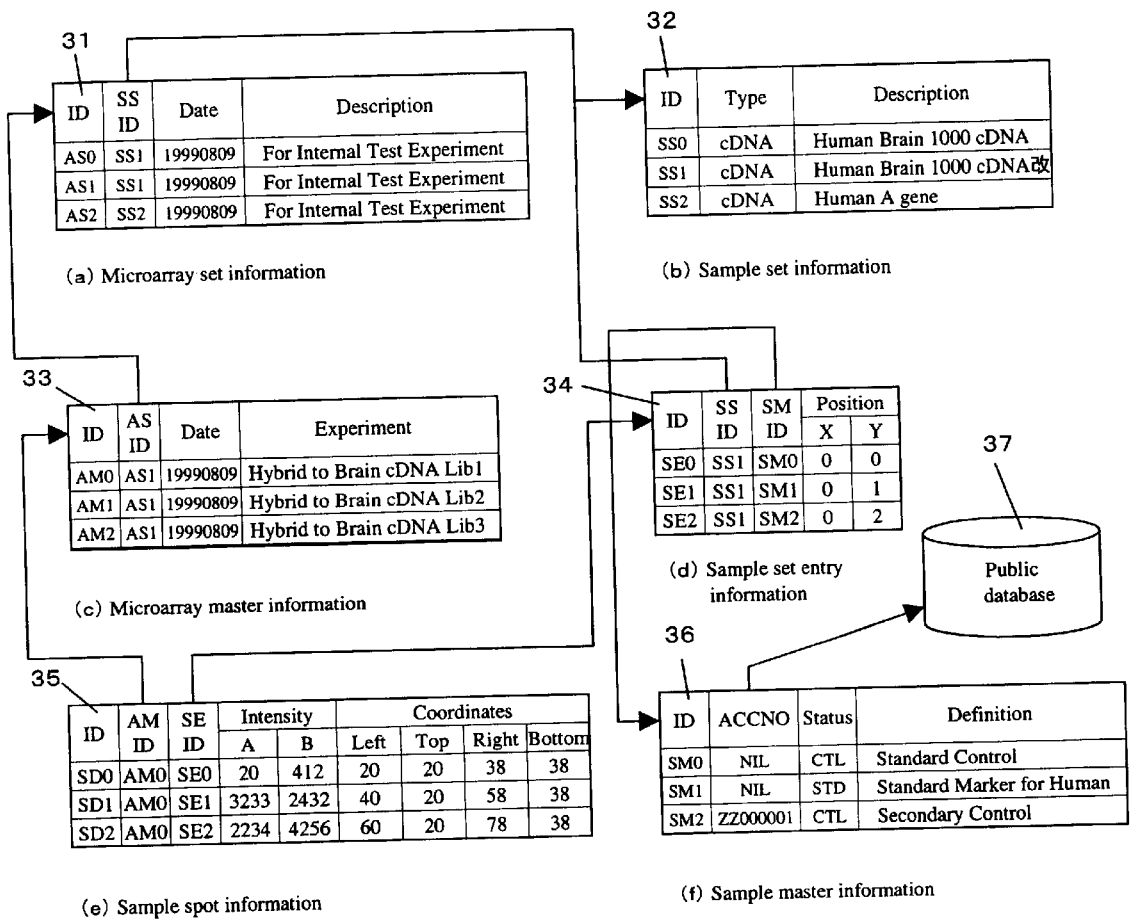
FIG. 3 is a diagram showing exemplary data structures of a microarray primary database.

FIG. 3 is a illustration showing exemplary data structure of the microarray primary database 23 shown in FIG. 2. This data structure are only shown as an example, and data structures different from that shown in FIG. 3 can also be employed.

As the data structure for storing various kinds of data for processing microarray information, (a) microarray set information, (b) sample set information, (c) microarray master information, (d) sample set entry information, (e) sample spot information and (f) sample master information are defined. In order to refer to the data records defining each data structure, unique data record IDs 31 to 36 are provided through the entire system as data record identifiers.

The information of the samples to be spotted on the microarray is stored in the database as data records of the sample master information shown in FIG. 3(f). For samples that are known to be present as entries in a public database 37 of DNA sequences and primary sequences of proteins, their Accession Nos. (ACCNO.) (used as reference numerals in the public database 37) can be stored in the microarray primary database 23 as a part of the sample master information so that further details of the samples can be acquired from the public database 37 as necessary.

The sample set information shown in FIG. 3(b) is defined as a data structure for storing information of a collection of samples that are to be spotted on the microarrays 10 for microarray production by the microarray producing apparatus 21. The sample set information includes the molecular types and descriptions of the sample collection.

Information of these samples (as constituent elements of the sample collection) are stored as data records (whose number corresponds to the number of elements) defined as the sample set entry information shown in FIG. 3(d) while correlating their data record IDs to the data records of the sample set information shown in FIG. 3(b) and to the data records of the sample master information shown in FIG. 3(f).

In view of performing a series of microarray experiments, the microarray producing apparatus produces a plurality of microarrays having the same sample set. The microarray set information shown in FIG. 3(a) is defined as a data structure for storing information of the collection of microarrays (the microarray set) while correlating their data record IDs to the sample set employed for the microarray set. The microarray set information further includes descriptions of the microarray set.

The microarray master information shown in FIG. 3(c) is defined as a data structure for storing information relative to individual microarrays 10, and includes data record IDs correlating to the microarray set they belong and information of microarray experiments.

The sample spot information shown in FIG. 3(e) is defined as a data structure for storing measurement values of individual sample spots resulting from the microarray experiments. The data records of the sample spot information are stored with data record IDs correlating to the data records of the microarray master information they belong and to the data records of the sample set entry information. The data records of the sample information also includes information of the physical positions of the sample spot regions on the microarray and accumulated luminescent intensities on the spot regions obtained with the measuring instrument.

Figure 4:
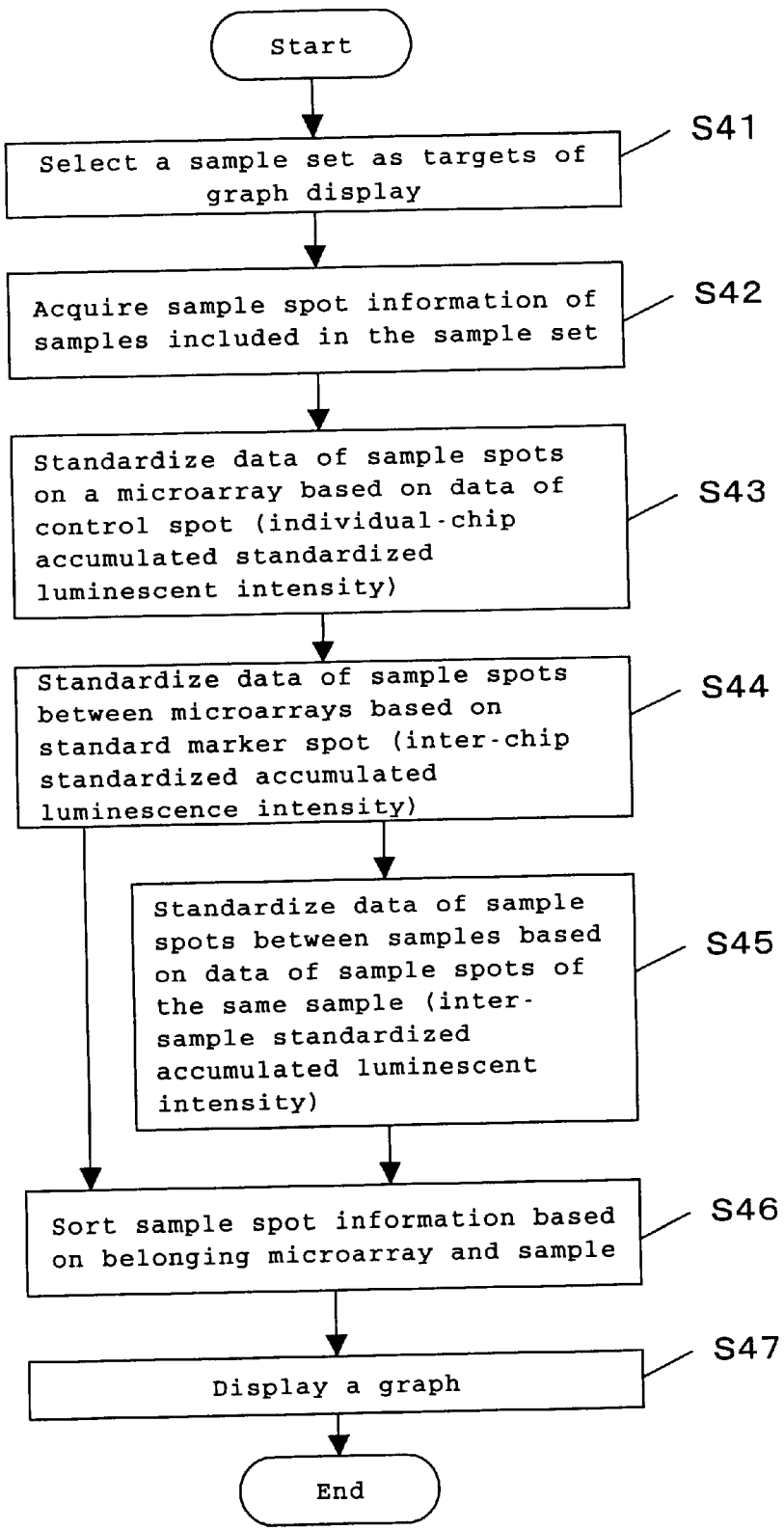
FIG. 4 is a flowchart of a process for producing data for displaying a graph.

FIG. 4 is a flowchart of a process in the system for displaying microarray information, for producing data for displaying a graph. Steps 41 to 45 in FIG. 4 are performed by the microarray data extracting/processing program 24 shown in FIG. 2, and steps 46 and 47 are performed by the microarray graph displaying program 26 shown in FIG. 2.

At Step 41, the microarray data extracting/processing program 24 first selects a set of samples as the subjects of the test. The sample set is selected from the data records of the sample set information in the microarray primary database 23. Next, at Step 42, information of sample spots corresponding to the samples included in the sample set is acquired as the data records of the sample spot information in the microarray primary database 23. The data records of the sample spot information are acquired, with reference to the data record IDs, in association with the data entries of the sample set information via the data records of the sample set entry information in the microarray primary database 23.

Herein, standardized accumulated luminescent intensities are obtained based on an actual value calculation. At Step 43, a first step of standardization is carried out for each sample spot for the purpose of eliminating experimental errors on individual microarrays. Specifically, the accumulated luminescent intensity of the control spot on the microarray is subtracted from the accumulated luminescent intensity of each sample spot, thereby obtaining individual-chip standardized accumulated luminescent intensities.

Next, a second step of standardization is carried out at Step 44 for the purpose of eliminating experimental errors between the microarrays and equalizing intentionally adjusted luminescent intensity ranges. For each sample spot, an individual-chip standardized accumulated luminescent intensity of an accumulated luminescent intensity of the standard marker spot on the belonging microarray is acquired and used for dividing the individual-chip standardized accumulated luminescent intensity of each sample spot, thereby obtaining inter-chip standardized accumulated luminescent intensities.

A third step of standardization is carried out as an option at Step 45 for the purpose of eliminating a difference of the luminescent intensities between the samples. The inter-chip standardized accumulated luminescent intensities of the sample spots are collected for each of the sample they belong, from which a top value is obtained and used to divide the inter-chip standardized accumulated luminescent intensities of the collected sample spots belonging to the same sample, thereby obtaining inter-sample standardized accumulated luminescent intensities.

The standardized accumulated luminescent intensities of the generated sample spots are sent to the microarray graph displaying program 26 via the display data cache 25. At Step 46, the microarray graph displaying program 26 collects and sorts the sample spots for each microarray. The collected sample spots are sorted such that the orders of the samples are the same. The microarrays may be sorted based on, for example, types of experiments. The samples may be sorted based on, for example, a standard deviation of the standardized accumulated luminescent intensities. Proceeding to Step 47, a graph is displayed based on the data of the standardized and sorted sample spots.

Figure 5:
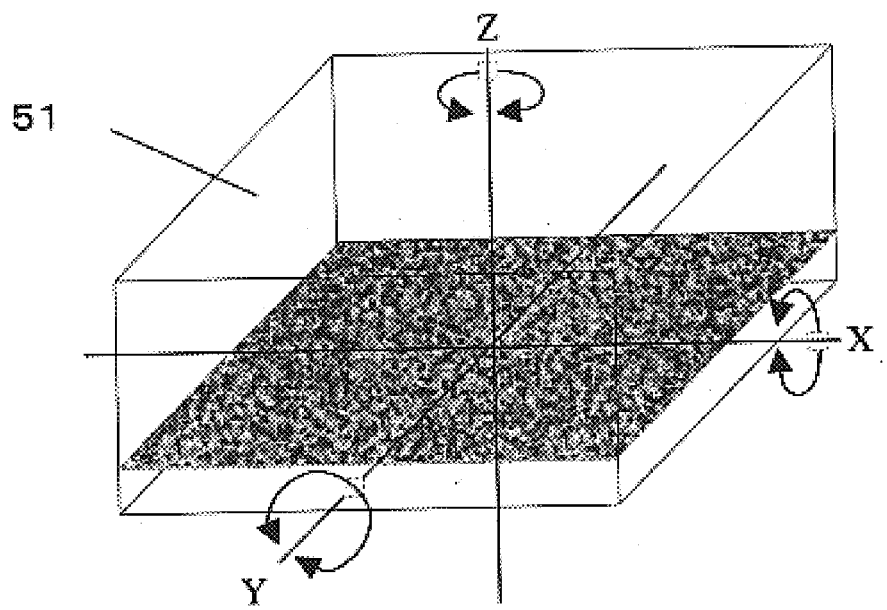
FIG. 5 shows diagrams illustrating a general idea of an example of producing a three-dimensional graph.
Figure 5:
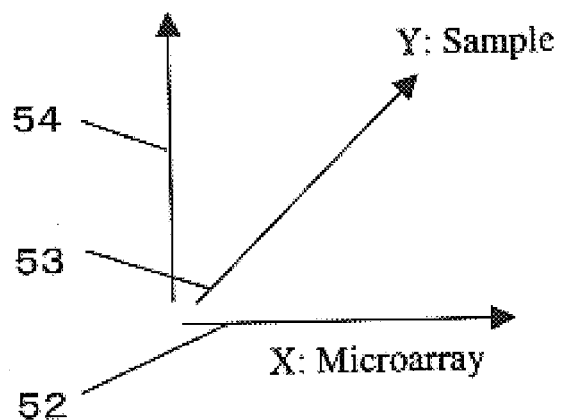

FIG. 5 shows diagrams illustrating a general idea of the three-dimensional graph displayed at Step 47 in FIG. 4. The microarrays and the samples sorted by the microarray graph displaying program 26 are plotted along the X-axis 52 or the Y-axis 53 in the three-dimensional graph 51. The standardized accumulated luminescent intensities calculated by the microarray data extracting/processing program 24 are plotted along the Z-axis 54. The microarrays and the samples range from 1 to the number of the elements. The standardized accumulated luminescent intensities range from 0 to 1.0000.

Coordinates of each sample spot are obtained and plotted on the three-dimensional graph based on the microarray, the sample and the standardized accumulated luminescent intensity of the sample spot. For plotting the sample spot coordinates, dots are sketched at the coordinates or a line is drawn between the coordinates where the Z-values are set to 0. The color of the dots or line is determined according to the Z-values of the sample spot coordinates, based on the settings on the three-dimensional graph display user interface which will be described later. When a range of the coordinate values on the Z-axis of the three-dimensional graph display is set with upper/lower limits on the three-dimensional graph display user interface, dots or a line that exceeds the limited range is not plotted. The resolutions of the X- and Y-axes can be selected. When the number of elements forming the X- or Y-axis exceeds the resolution, a plurality of elements are spotted as a single element on the graph. In this case, the Z-value of the plurality of elements may be any one of the top, bottom or average value. In addition, lines may optionally be drawn between the top and bottom values upon linear plotting.

In order to prevent the display of the three-dimensional graph from being unclear due to the overlapping of the information forming the graph, the three-dimensional graph is made rotatable around each of the X-, Y- and Z-axes. Furthermore, colors may be changed, on the three-dimensional setting user interface, according to the function of re-sketching a difference within particular X- and Y-axes ranges as the graph ranges and according to the values of the Z-axis, whereby a characteristic sample spot information can readily be confirmed.

Figure 6:
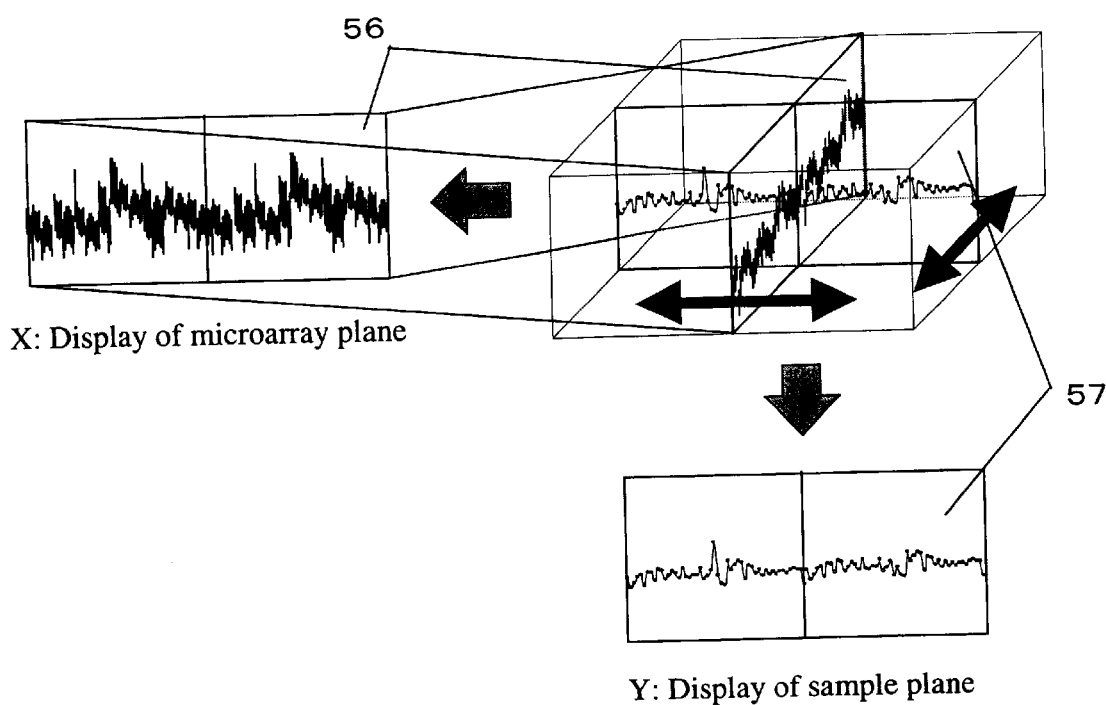
FIG. 6 shows exemplary two-dimensional graphs obtained by slicing the three-dimensional graph.

As shown in FIG. 6, a two-dimensional graph 56 obtained by slicing the three-dimensional graph with respect to the X-axis and a two-dimensional graph 57 obtained by slicing the three-dimensional graph with respect to the Y-axis are displayed for a designated sample spot.

Figure 7:
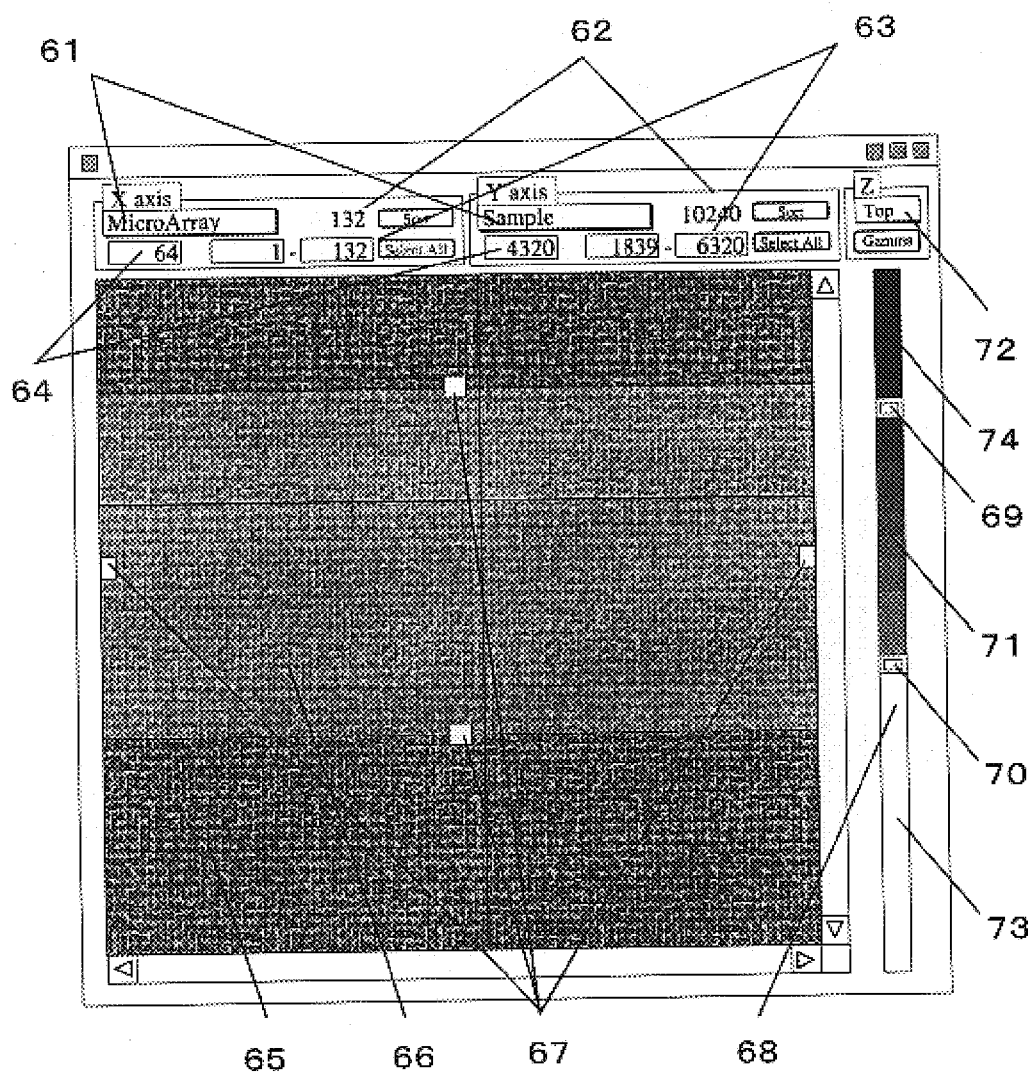
FIG. 7 is a view showing an exemplary interface for a user to perform settings to display a graph.

FIG. 7 is a view showing an exemplary user interface which dynamically performs the settings of the three-dimensional graph display.

Based on the settings of the items 61 to be plotted along the X- and Y-axes (in the figure, X-axis represents the microarrays while the Y-axis represents the samples), numbers of the elements are given in the display sections 62 (in the figure, the number of elements along the X-axis is 132 while the number of elements along the Y-axis is 10240), whereby the ranges 63 for displaying the three-dimensional graph can be determined. A subject of the two-dimensional graph display is designated by determining specific elements along the respective axes in boxes 64.

In the display section 65 under the user interface, individual sample spots obtained by slicing the three-dimensional graph with respect to the Z-axis and seen in the Z-axis direction are displayed as image information. The ranges of the elements forming the X- and Y-axes to be displayed on the three-dimensional graph can be determined in boxes 63, are displayed on the image information (66), and can be altered by using handles 67. Pixels forming the image information correspond to Z-axis values. A pixel color information interface 68 is provided for setting which value to be displayed with which color. In the pixel information interface, as an interface for converting an actual value to a color, a button 69 for setting the minimum value to be used for color graduation and a button 70 for setting the maximum value to be used for color graduation are provided to produce a color list 71 for assigning colors to the actual values within that range. The color list is a sequence of sequential color information to which any particular number of elements can be input. The actual values within the maximum and minimum values to be used for color graduation are assigned to respective color entries at regular intervals or by a gamma function or by free setting. The resolution of the screen for displaying the image information can be set by the user and is the same resolution as the three-dimensional graph. When the number of the elements exceeds the resolution, a plurality of elements are processed as a single element. In this case, the actual value or Z-value is selected from the top, bottom or average value of the plurality of elements with a selection button 72 of the interface or on the three-dimensional graph display. Pixels of values 73 lower than the minimum value to be used for color graduation and pixels of values 74 higher than the maximum value to be used for color graduation may be selected to be displayed as entries at the ends of the color list or may not be displayed.

Figure 8A:
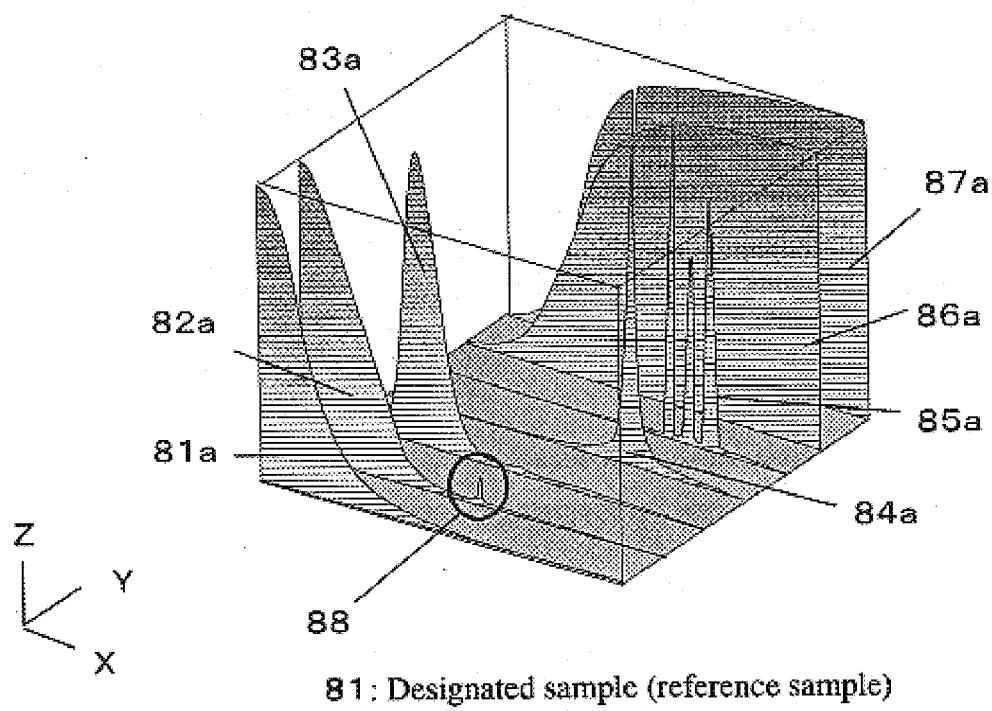
FIGS. 8(a) and 8(b) are diagrams showing an exemplary comparison of expression profiles by using a three-dimensional graph display of the invention.
Figure 8B:
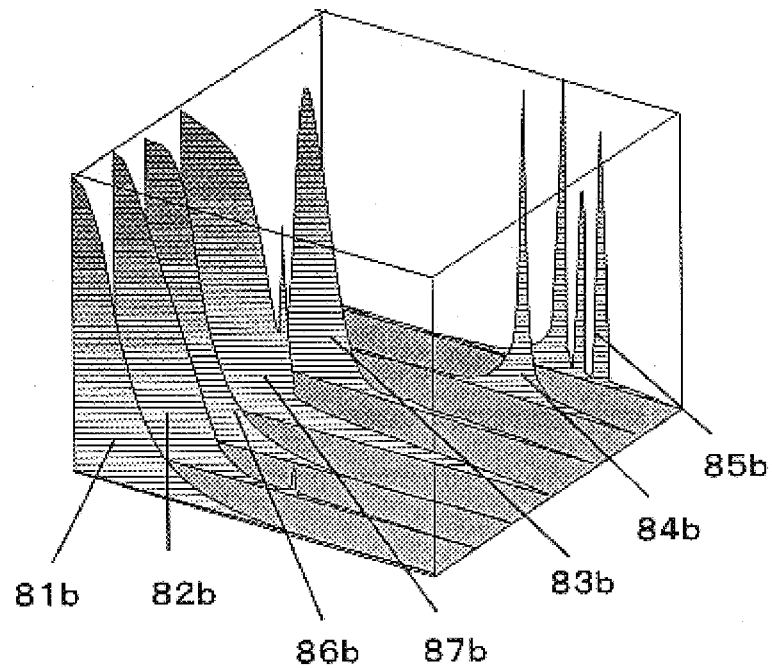

FIGS. 8(a) and 8(b) are diagrams showing an exemplary comparison of expression profiles by using a three-dimensional graph display of the invention. For a collection of cDNA-library-immobilized microarrays having already reacted (hybridized) cDNA collection as subjects of experiments, inter-sample standardized accumulated luminescent intensities of the sample spots are obtained according to the procedure of the invention to display a three-dimensional graph. Samples 81a, 82a, 83a, . . . shown in FIG. 8(a) correspond to samples 81b, 82b, 83b, . . . shown in FIG. 8(b), respectively.

FIG. 8(a) is a diagram where, with respect to one designated sample (a reference sample) 81, the elements of the microarray-axis (X-axis) and the elements of the sample-axis (Y-axis) are sorted according to the luminescent intensity of the sample and according to a sum of squares of the difference between an inter-sample standardized accumulated luminescent intensities of the designated sample and that of each sample (according to the value for each microarray), respectively. Based on this three-dimensional graph, samples 82, 83, 86 and 87 which have expression profiles similar to that of the designated sample 81 can readily be found. Specifically, the samples 82, 83, 86 and 87 having the expression profiles relative to that of the selected sample 81 are represented by smooth curves in the three-dimensional graph. A slightly different feature 88 of the sample 82 with the expression profile similar to that of the sample 81 can also be easily specified.

FIG. 8(b) is a diagram where the sample-axis (Y-axis) is sorted according to a sum of squares of a difference between a mean deviation of the inter-sample standardized accumulated luminescent intensities of sample spots belonging to each type of sample and a mean deviation of the inter-sample standardized accumulated luminescent intensities of the designated sample 81. According to this three-dimensional graph, samples 86 and 87 whose expressions are controlled under the same conditions but with different types of expression enhancement and suppression can readily be found.

INDUSTRIAL APPLICABILITY

As described above, according to the present invention, huge amount of sample spot information obtained by microarray experiments is standardized so that the whole information can be processed in an equalized fashion. Therefore, data can easily be compared and can be displayed as graphs in various respects. As a result, rare but important information can be found from the huge amount of information.

What is claimed is:

1. A method for displaying microarray information via a three-dimensional graph by which information of accumulated luminescent intensities of numerous sample spots obtained by a microarray analysis is displayed, the method comprising the steps of:

selecting a set of samples as subjects of tests under different conditions;

spotting the same set of samples on each of a plurality of microarrays each for performing one of the tests;

acquiring accumulated luminescent intensities of the sample spots on each of the plurality of microarrays, the sample spots correspond to the same set of samples;

sorting the sample spots on each of the plurality of microarrays in an identical manner and/or the plurality of microarrays to which the sample spots belong under predetermined conditions; and displaying a three-dimensional graph by assigning the sample spots sorted in the sorting step to a first axis and the microarrays sorted in the sorting step to a second axis, and the accumulated luminescent intensities to a third axis, wherein the first, second and third axes define the three-dimensional graph.

2. A method for displaying microarray information according to claim 1, wherein the accumulated luminescent intensities are based on standardized luminescent intensities which have undergone a first standardization using a control spot located on each microarray for a purpose of eliminating experimental errors within the microarray to which the sample spot belongs, and a second standardization using a standard marker spot located on each microarray for the purpose of eliminating experiment errors between the microarrays and for the purpose of equalizing an intentionally adjusted range of luminescent intensities.

3. A method for displaying microarray information according to claim 2, wherein the standardized accumulated luminescent intensities have undergone, in addition to the first and second standardizations, a third standardization in view of the luminescent intensity ranges between the samples based on the accumulated luminescent intensities of the sample spots belonging to the same sample.

4. A method for displaying microarray information according to any one of claims 1 to 3, wherein the set of samples are sorted according to their accumulated luminescent intensities on a specific microarray.

5. A method for displaying microarray information according to any one of claims 1 to 3, wherein the set of samples are sorted according to their accumulated luminescent intensities on a specific microarray, and then the plurality of microarrays are sorted according to a total difference of the accumulated luminescent intensities of their samples from that of the specific microarray.

6. A method for displaying microarray information according to any one of claims 1 to 3, wherein the plurality of microarrays are sorted according to an accumulated luminescent intensity of a specific sample.

7. A method for displaying microarray information according to any one of claims 1 to 3, wherein the plurality of microarrays are sorted according to an accumulated luminescent intensity of a specific sample, and then the set of samples are sorted according to a total difference of the accumulated luminescent intensities on the microarrays from that of the specific sample.

8. A method for displaying microarray information, wherein a two-dimensional graph is displayed by slicing out a cross-sectional plane from the three-dimensional graph displayed by the method for displaying microarray information according to any one of claims 1 to 3.

* * * * *